US005437652A

United States Patent [19]

Anatolievich

[11] Patent Number: 5,437,652

[45] Date of Patent: Aug. 1, 1995

[54] DEVICE FOR COLLECTING SPERM

[76] Inventor: Pomozov P. Anatolievich, ul. Kavkazski Bulevard 35 kv. 329, 115516 Moscow, Russian Federation

[21] Appl. No.: 140,447

[22] Filed: Oct. 25, 1993

[30] Foreign Application Priority Data

Apr. 3, 1993 [RU] Russian Federation ............ 3011525

[51] Int. Cl.[6] ............ A61F 5/44

[52] U.S. Cl. ............ 604/349

[58] Field of Search ............ 128/760, 767, 842–844; 604/346, 347, 349, 353

[56] References Cited

U.S. PATENT DOCUMENTS 4,312,350 1/1982 Doan ............ 604/349
4,906,242 3/1990 Thomas ............ 604/353
5,205,298 4/1993 Hurst ............ 128/842

FOREIGN PATENT DOCUMENTS 0441934 9/1974 Russian Federation ............ 604/349
1015891 5/1983 U.S.S.R. ............ 604/349

*Primary Examiner*—Max Hindenburg
*Attorney, Agent, or Firm*—Ilya Zborovsky

[57] ABSTRACT

A device for collecting sperm includes a sperm collecting receptacle, an elastic element having an interior which receives a penis and communicates with the sperm collecting receptacle, and a compressed air source which supplies compressed air to periodically compress the elastic element and the penis inside the latter, to cause ejaculation and supply of the sperm into the sperm collecting receptacle.

9 Claims, 1 Drawing Sheet

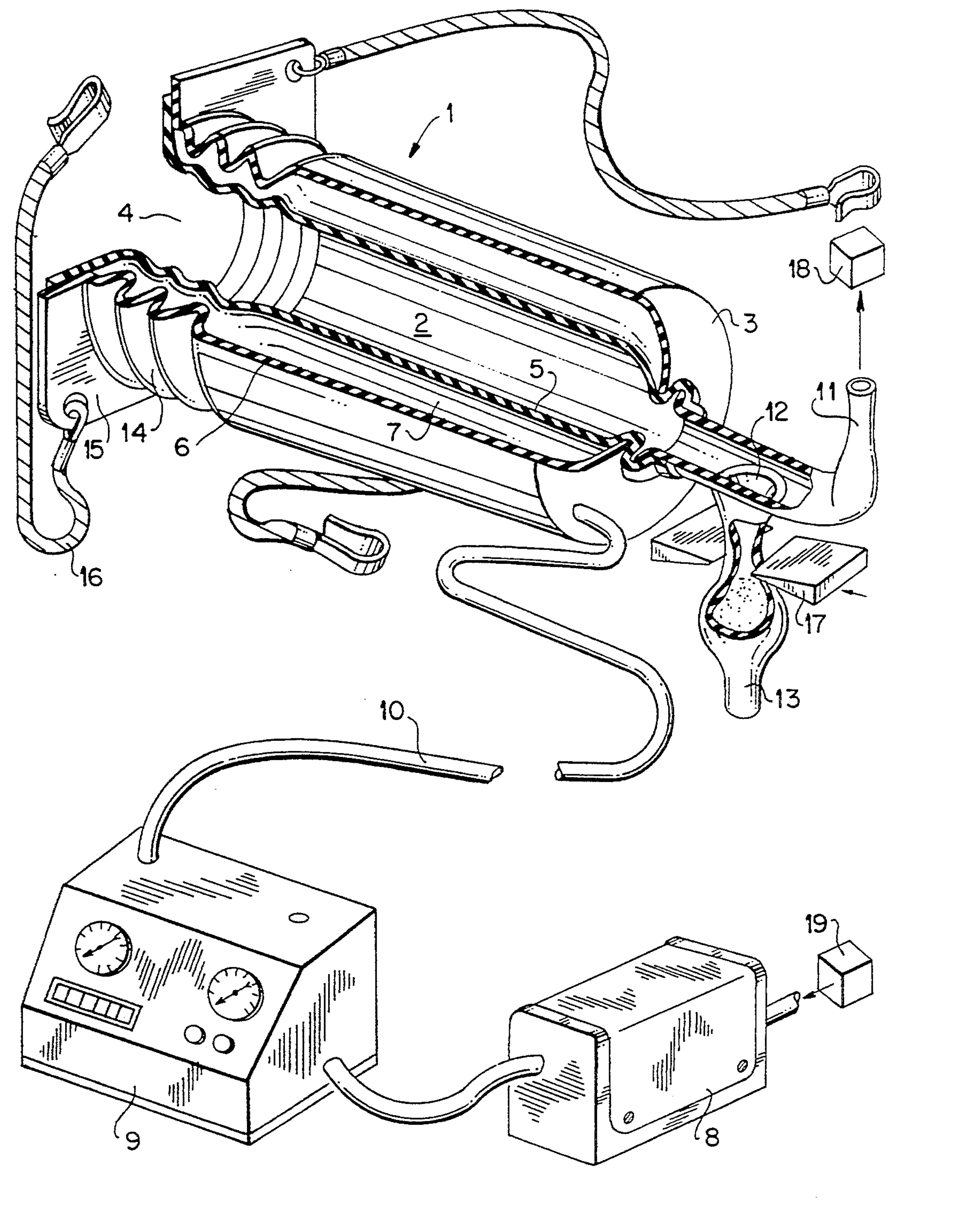
1
4
2
3
18
5
11
12
15
14
6
7
16
17
13
10
19
9
8

DEVICE FOR COLLECTING SPERM

BACKGROUND OF THE INVENTION

The present invention relates to a device for collecting sperm. It can be used in endocrinology, genetic research, obstetrics and gynecology and other areas of medicine in which collection of sperm is needed.

Known method of collecting sperm are generally primitive and inefficient. A manual method is highly undesirable because of psychogenic factors of patients. A single device for collecting sperm is disclosed in A. N. Lazarenko and O. V. Lifshitz, "Obtaining the Sperm by Method of Vibroejaculation", in "Works of the Moscow Research Institute for Phychiatry of the Health Ministry of the Russian Federation", 1972, vol.65, p.p.216–222. This device has a vibrator with a plastic glass fixed to one of its nozzles. The penis is placed into the glass, the vibrator is switched on, and the vibration causes erection and further ejaculation. The sperm is collected on the bottom of the glass. While the device has obvious advantages when compared with the manual method, it still possesses some disadvantages. It has been determined that with some patients the vibrations caused by the vibrator do not produce the required reaction for obtaining erection and subsequent ejaculation. Also, the device operates with a process which is performed under aphysiological conditions. It is to be understood that therefore it is advisable to provide new and more efficient devices of this type.

SUMMARY OF THE INVENTION

Accordingly, it is an object of the present invention to provide a device for collecting sperm which avoids the disadvantages of the prior art and provides for highly advantageous results.

In keeping with these objects and with others which will become apparent hereinafter one feature of the present invention resides, briefly stated, in a device for collecting sperm, which has a sperm collecting receptacle, and elastic element formed to receive a penis and having an interior communicating with the sperm collecting receptacle, and means for supplying compressed air to said elastic element so as to periodically compress the elastic element and thereby to periodically compress the penis received in the elastic element to cause erection of the penis and ejaculation.

The novel features of the present invention are set forth in the appended claims. The invention itself, however, both as to its construction and its manner of operation, will be best understood from the following description of preferred embodiments which is accompanied by the following drawings.

BRIEF DESCRIPTION OF THE DRAWINGS

The single FIGURE of the drawings is a view showing a device for collecting sperm in accordance with the present invention, in perspective.

DESCRIPTION OF PREFERRED EMBODIMENTS

A device for collecting sperm in accordance with the present invention has an elastic cylindrical element 1 which forms an inner chamber 2 for receiving a penis. The chamber 2 is closed at one end 3 and open at another end 4. The elastic element is double-walled and has an inner wall 5 and an outer wall 6 which form a cavity 7 therebetween. The inner wall 5 is removable. A blower 19 supplies compressed air through a heater 8, an air control 9, and a conduit 10 into the cavity 7 through the closed end 3 of the elastic element 1. A nozzle 11 communicates with the cavity 7 and discharges the air from the latter by a suction pump 18.

The nozzle 11 is provided with an opening 12 which communicates with a removable sperm receptacle formed for example as a bag 13. The portion of the elastic element 1 which adjoins the open end 4 is corrugated as identified with reference numeral 14. It is connected with a removable flange 15. The device is further provided with means 16 for fixing the device to a human body, and thermocutting members 17.

The device for collecting sperm in accordance with the present invention operates in the following manner:

The sterile inner wall 5 and the flange 15 are installed into the device. The cavity 7 is filled with air. The penis is introduced into the inner chamber 2 of the elastic element 1. The device is fixed on the patient by the fixing means 16. Then the compressed air is supplied periodically by pulses into the cavity 5 so as to provide, for example, 10–20 compression of the penis per 1 minute. It has been found that approximately in 10 minutes the ejaculation begins. After this, the suction pump 18 is actuated and the blower 19 is turned off, and the suckled air provides a momentary supply of the sperm through the hole 12 into the sperm collector 13. The thermocutters approach each other to fuse the collector 13 so as to close it and then severe from the device.

The pulsating supply of the compressed air is performed in a known manner by the control device 9 which is formed as an air frequency generator which supplies air into the chamber 7 with a desired frequency. The outer wall 6 of the elastic element 1 can be made less elastic than the inner wall 5 to direct the compressions inwardly.

It will be understood that each of the elements described above, or two or more together, may also find a useful application in other types of devices differing from the types described above.

While the invention has been illustrated and described as embodied in a device for improving erection, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A device for collecting sperm, comprising
a sperm collecting receptacle;
an elastic element formed to receive a penis and having an interior communicating with an interior of said sperm collecting receptacle;
means for supplying compressed air periodically to said elastic element so as to cause periodical compressions of said elastic element and thereby periodical compressions of the penis in said elastic element to cause ejaculation and sperm supply into said sperm collecting receptacle; and a nozzle for withdrawing air from said elastic element, said nozzle being provided with an opening communicating with the interior of said sperm collecting receptacle to provide the sperm supply to the latter during air withdrawal from said elastic element through said nozzle.

2. A device for collecting sperm as defined in claim 1, wherein said elastic element has an inner wall which limits said interior of said elastic element and an outer wall spaced from said inner wall to form a cavity between said walls, said compressed air supplying means being connected with and supplying the compressed air into said cavity between said walls.

3. A device for collecting sperm as defined in claim 2, wherein said inner wall is removable from said outer wall, so that said inner wall can be removed and replaced with a new such inner wall for a new patient, to privide sterile collection of sperm without risk of transmission of infections between patients.

4. A device for collecting sperm as defined in claim 1, wherein said elastic element has one side which is connected with said sperm collecting receptacle and another side through which the penis is introduced into the interior of said elastic element, said other side has a corrugated portion to adjust a length of said elastic element to a length of the penis of the patient.

5. A device for collecting sperm as defined in claim 4; and further comprising a removable flange adapted to abut against a body of the patient and connected with said corrugated portion of said elastic element.

6. A device for collecting sperm as defined in claim 1, wherein said sperm collecting receptacle is formed as a small bag composed of a synthetic plastic material.

7. A device for collecting sperm as defined in claim 1; and further comprising means for fixing said elastic element to a body of the patient.

8. A device for collecting sperm as defined in claim 1; and further comprising means for closing said sperm collecting receptacle after receiving the sperm in it, and removing the closed sperm collecting receptacle from said elastic element.

9. A device as defined in claim 8, wherein said closing and removing means includes a thermocutting unit.

* * * * *